United States Patent [19]

Grindstaff

[11] Patent Number: 5,153,324
[45] Date of Patent: Oct. 6, 1992

[54] PROCESS FOR PREPARING SULFONYLUREAS

[75] Inventor: Teddy H. Grindstaff, Charleston, W. Va.

[73] Assignee: E. I. du Pont de Nemours and Company, Wilmington, Del.

[21] Appl. No.: 814,341

[22] Filed: Dec. 26, 1991

[51] Int. Cl.⁵ ............... C07D 239/42; C07D 239/48; C07D 251/46; C07D 251/52

[52] U.S. Cl. .................... 544/211; 544/212; 544/208; 544/209; 544/206; 544/207; 544/320; 544/321; 544/324; 544/323; 544/331; 544/332

[58] Field of Search ............... 544/211, 212, 208, 209, 544/206, 207, 320, 321, 324, 323, 331, 332

[56] References Cited

U.S. PATENT DOCUMENTS 4,127,405  11/1978  Levitt ..................... 71/93

*Primary Examiner*—John M. Ford

[57] ABSTRACT

A process for preparing herbicidal sulfonylureas which comprises mixing a sulfonylisocyanate and a heterocyclic amine in the absence of a solvent.

10 Claims, No Drawings

PROCESS FOR PREPARING SULFONYLUREAS

FIELD OF THE INVENTION

A process for preparing herbicidal sulfonylureas which comprises the coupling of a sulfonylisocyanate and a heterocyclic amine in the absence of a solvent.

BACKGROUND OF THE INVENTION

Sulfonylurea herbicides are an extremely potent class of herbicides discovered relatively recently which generally consist of a sulfonylurea bridge, —$SO_2NHCONH$—, linking two aromatic or heteroaromatic ring structures. Such herbicides have become commercially important. There is therefore a continuing need to discover new processes for their preparation that offer advantages that add to their commercial desirability.

SUMMARY OF THE INVENTION

The present invention is a novel process for the preparation sulfonylurea herbicides of Formula I

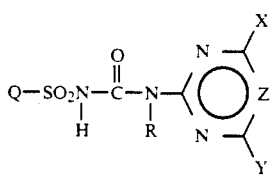

wherein:
Q is selected from the group

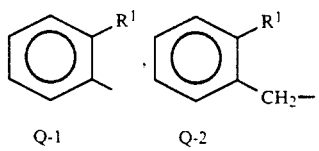

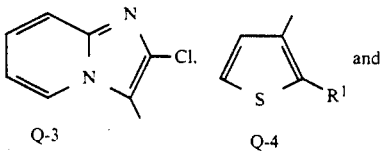

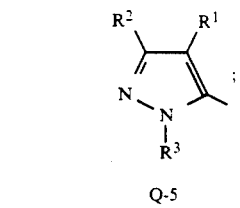

X is selected from the group Cl, $CH_2$, $OCH_3$, $OCH_2CH_3$ and $OCHF_2$;
Y is selected from the group $CH_3$, $OCH_3$, $OCHF_2$ and $NHCH_3$;
Z is selected from the group N and CH;
R is selected from the group H and $CH_3$;
$R^1$ is selected from the group Cl, $CO_2CH_3$, $CO_2CH_2CH_3$, $OCH_2CH_2Cl$ and $OCH_2CH_2OCH_3$;
$R^2$ is selected from the group H and Cl; and
$R^3$ is selected from the group $CH_3$ and 2-pyridinyl; which comprises reacting a sulfonylisocyanate of Formula II $$Q-SO_2NCO \quad II$$

with an amine of Formula III

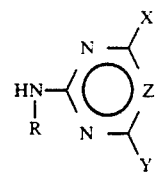

in the absence of a solvent.

Typically, the reaction is carried out by mixing equimolar quantities of isocyanate and amine, under an inert atmosphere, with the exclusion of moisture. The mixture is placed in a grinder, e.g., a ball mill, and allowed to mix at a temperature of about 20° to 90° C. until a homogenous amorphous solid is obtained, usually less than 3 hours. The preferred temperature is that temperature at which the isocyanate component is liquid. This aids in the mixing process. The use of other than equimolar quantities results in a lower conversions with greater yields of undesirable by-products. Owing to the reactivity of the isocyanate components with water, rigorous exclusion of moisture yields higher conversions and again less undesirable by-product formation. The formation of undesirable by-products results in final products of lower purity. Thus, for reasons of economy and purity of final products, the instant process is best carried out using equimolar quantities of reactants and conducting the process under anhydrous conditions.

The preferred processes of the invention which yield the indicated products are:

1. The process wherein Q is Q-1, $R^1$ is Cl, R is H, X is $CH_3$, Y is $OCH_3$ and Z is N, the resulting product is chlorsulfuron.
2. The process wherein Q is Q-1, $R^1$ is $CO_2CH_3$, R is H, X is $CH_3$, Y is $OCH_3$ and Z is N, the resulting product is metsulfuron methyl.
3. The process wherein Q is Q-1, $R^1$ is $CO_2CH_3$, R is $CH_3$, X is $CH_3$, Y is $OCH_3$ and Z is N, the resulting product is tribenuron methyl.
4. The process wherein Q is Q-1, $R^1$ is $CO_2CH_3$, R is H, X is $CH_3$, Y is $CH_3$ and Z is CH, the resulting product is sulfometuron methyl.
5. The process wherein Q is Q-1, $R^1$ is $CO_2CH_3$, R is H, X is $OCH_2CH_3$, Y is $NHCH_3$ and Z is N, the resulting product is ethametsulfuron methyl.
6. The process wherein Q is Q-1, $R^1$ is $CO_2CH_2CH_3$, R is H, X is Cl, Y is $OCH_3$ and Z is CH, the resulting product is chlorimuron methyl.
7. The process wherein Q is Q-1, $R^1$ is $OCH_2CH_2Cl$, R is H, X is $CH_3$, Y is $OCH_3$ and Z is N, the resulting product is triasulfuron.
8. The process wherein Q is Q-1, $R^1$ is $OCH_2CH_2OCH_3$, R is H, X is $OCH_3$, Y is $OCH_3$ and Z is N, the resulting product is cinosulfuron.
9. The process wherein Q is Q-1, $R^1$ is $CO_2CH_3$, R is H, X and Y are $OCHF_2$ and Z is CH, the resulting product is primisulfuron methyl.
10 The process wherein Q is Q-2, $R^1$ is $CO_2CH_3$, R is H, X is $OCH_3$, Y is $OCH_3$ and Z is CH, the resulting product is bensulfuron methyl.

11. The process wherein Q is Q-3, R is H, X is OCH$_3$, Y is OCH$_3$ and Z is CH, the resulting product is imazosulfuron (proposed common name).
12. The process wherein Q is Q-4, R$^1$ is CO$_2$CH$_3$, R is H, X is CH$_3$, Y is OCH$_3$ and Z is N, the resulting product is thifensulfuron methyl.
13. The process wherein Q is Q-5, R$^1$ is CO$_2$CH$_2$CH$_3$, R$^2$ is H, R$^3$ is CH$_3$, R is H, X is OCH$_3$, Y is OCH$_3$ and Z is CH, the resulting product is pyrazosulfuron ethyl.
14. The process wherein Q is Q-5, R$^1$ is CO$_2$CH$_3$, R$^2$ is Cl, R$^3$ is CH$_3$, R is H, X is OCH$_3$, Y is OCH$_3$ and Z is CH.
15. The process wherein Q is Q-5, R$^1$ is CO$_2$CH$_3$, R$^2$ is H, R$^3$ is 2-pyridinyl, R is H, X is CH$_3$, Y is CH$_3$ and Z is CH.

The products indicated above as being produced by the process of the invention are all known herbicides.

DETAILED DESCRIPTION OF THE INVENTION

The process of the present invention proceeds according to the following Equation 1.

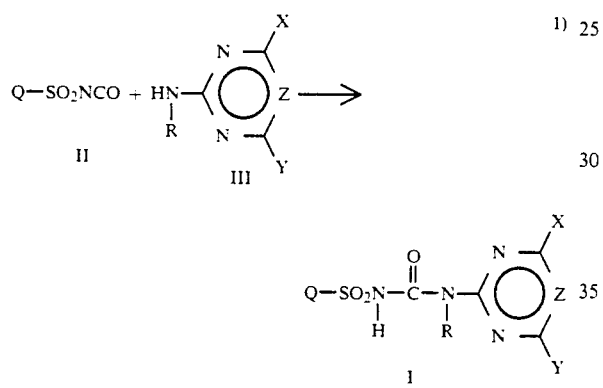

wherein Q, R, X, Y and Z are as defined above.

Typically, the process is carried out by mixing equimolar quantities of sulfonylisocyanate and amine, under an inert atmosphere. The mixture is placed in a grinder, such as a ball mill, and allowed to mix at a temperature of about 20° to 90° C. and a pressure of 1 to 5 atmospheres until a homogenous amorphous solid is obtained, usually 0.1 to 2 hours.

A key aspect for successful, high yield coupling is the efficient mixing afforded by use of a milling device. A premixing of the sulfonylisocyanate and amine reactants can be carried out using a mortar and pestle or a mechanical mixing device. Once mixed, the mixture is milled in a grinding device, such as a ball mill grinder, to promote thorough mixing which results in a solid amorphous product.

The preferred temperature is that temperature at which the sulfonylisocyanate is liquid. The preferred pressure is 1 atmosphere.

The sulfonylisocyantes of Formula II and the heterocyclic amines of Formula III are known and are easily prepared and coupled in the presence of a solvent to provide compounds of Formula I by the procedures described in U.S. Pat. No. 4,127,405, U.S. Pat. No. 4,379,769, U.S. Pat. No. 4,383,113, U.S. Pat. No. 4,394,506, U.S. Pat. No. 4,238,621, U.S. Pat. No. 4,547,215, U.S. Pat. No. 4,420,325, U.S. Pat. No. 4,454,334, U.S. Pat. No. 4,740,234, U.S. Pat. No. 4,481,029, U.S. Pat. No. 4,548,638, U.S. Pat. No. 4,514,212, U.S. Pat. No. 4,478,635, U.S. Pat. No. 4,479,821, U.S. Pat. No. 4,994,571, U.S. Pat. No. 4,931,081, U.S. Pat. No. 4,705,558 and literature cited therein. Furtherthemore, these references teach the utility and formulation of compounds of Formula I.

A significant advantage of the instant solventless process is reduction of waste solvent which requires appropriate disposal or recycling. The instant coupling process doesn't employ a solvent and, as such, waste solvent handling is eliminated. Thus, the environmental problems associated with waste solvent handling are avoided.

The following example further illustrates the invention, but is not intended to limit it in any manner.

EXAMPLE 1

Preparation of Methyl-3-[[[[(4-Methoxy-6-Methyl-1,3,5-Triazine-2-yl)]Amino]Carbonyl]Amino]Sulfonyl]-2-Thiophenecarboxylate (Thifensulfuron)

With a mortar and pestle, 3.2 g of 2-amino-4-methoxy-6-methyl-1,3,5-triazine (0.023 moles) and 6.2 g of methyl-3-sulfonylisocyanato-2-thiophenecarboxylate (0.023 moles, approximately 90% pure) were mixed under an inert atmosphere. The mixture was placed in a U.S. Stoneware ball mill jar containing 2.2 cm diameter steel ball bearings. The jar was rotated at the maximum mill speed of 300 rpm and heated with a heat gun until the exterior surface temperature reached 110° C. (interior temperature approximately 75° C.). After 2 hours, 9.4 g of an amorphous solid was obtained, mp 172° C., which was determined by liquid chromatography to be 92.66% of the title compound.

What is claimed is:

1. A process for the preparation of sulfonylurea herbicides of Formula I

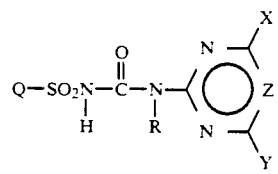

wherein:
Q is selected from the group

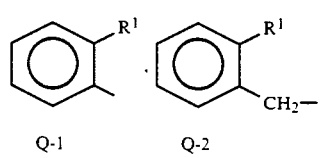

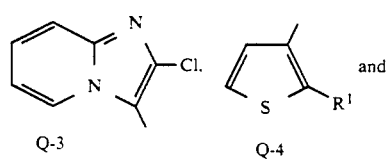

-continued

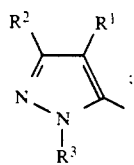

Q-5

X is selected from the group Cl, $CH_3$, $OCH_3$, $OCH_2CH_3$ and $OCHF_2$;

Y is selected from the group $CH_3$, $OCH_3$, $OCHF_2$ and $NHCH_3$;

Z is selected from the group N and CH;

R is selected from the group H and $CH_3$;

$R^1$ is selected from the group Cl, $CO_2CH_3$, $CO_2CH_2CH_3$, $OCH_2CH_2Cl$ and $OCH_2CH_2OCH_3$;

$R^2$ is selected from the group H and Cl; and $R^3$ is selected from the group $CH_3$ and 2-pyridinyl;

which comprises reacting a sulfonylisocyanate of Formula II $$Q-SO_2NCO \qquad II$$

with an amine of Formula III

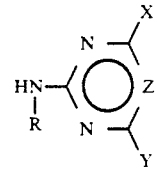

in the absence of a solvent by mixing the isocyanate and the amine under an inert atmosphere with the exclusion of moisture.

2. The process of claim 1 wherein Q is Q-1, $R^1$ is Cl, R is H, X is $CH_3$, Y is $OCH_3$ and Z is N.

3. The process of claim 1 wherein Q is Q-1, $R^1$ is $CO_2CH_3$, R is H, X is $CH_3$, Y is $OCH_3$ and Z is N.

4. The process of claim 1 wherein Q is Q-1, $R^1$ is $CO_2CH_3$, R is $CH_3$, X is $CH_3$, Y is $OCH_3$ and Z is N.

5. The process of claim 1 wherein Q is Q-1, $R^1$ is $CO_2CH_3$, R is H, X is $CH_3$, Y is $CH_3$ and Z is CH.

6. The process of claim 1 wherein Q is Q-1, $R^1$ is $CO_2CH_3$, R is H, X is $OCH_2CH_3$, Y is $NHCH_3$ and Z is N.

7. The process of claim 1 wherein Q is Q-1, $R^1$ is $CO_2CH_2CH_3$, R is H, X is Cl, Y is $OCH_3$ and Z is CH.

8. The process of claim 1 wherein Q is Q-2, $R^1$ is $CO_2CH_3$, R is H, X is $OCH_3$, Y is $OCH_3$ and Z is CH.

9. The process of claim 1 wherein Q is Q-4, $R^1$ is $CO_2CH_3$, R is H, X is $CH_3$, Y is $OCH_3$ and Z is N.

10. The process of claim 1 wherein Q is Q-5, $R^1$ is $CO_2CH_2CH_3$, $R^2$ is H, R is H, X is $OCH_3$, Y is $OCH_3$ and Z is CH.

* * * * *